United States Patent [19]

Greatbatch

[11] 4,291,125
[45] Sep. 22, 1981

[54] METHOD FOR ELECTRONIC CONTROL OF INFECTIONS USING SILVER IONS

[76] Inventor: Wilson Greatbatch, 5220 Donnington Rd., Clarence, N.Y. 14031

[21] Appl. No.: 112,704

[22] Filed: Jan. 16, 1980

[51] Int. Cl.³ .................. C12N 5/00; A01N 59/16
[52] U.S. Cl. ........................ 435/240; 47/1.3;
   47/DIG. 1; 204/131; 424/132; 435/241;
   435/284; 435/800
[58] Field of Search .................. 424/132; 204/131;
   435/240, 241; 47/1.3, DIG. 1

[56] References Cited

U.S. PATENT DOCUMENTS

| | | | |
|---|---|---|---|
| 2,121,875 | 6/1938 | Kruse et al. | 204/24 |
| 2,344,548 | 3/1944 | Goetz | 204/137 |
| 3,936,364 | 2/1976 | Middle | 426/66 |
| 4,184,974 | 1/1980 | Van Leuven | 252/106 |

OTHER PUBLICATIONS

Berger et al—Antimicrobial Agents and Chemotherapy, Nov. 1976, vol. 10, No. 5, pp. 856–860.

*Primary Examiner*—Leonard Schenkman
*Attorney, Agent, or Firm*—Christel, Bean & Linihan

[57] ABSTRACT

A method and apparatus for killing plant and animal bacteria and plant viroids by electrically generated silver ions. The silver ions serve as germicidal agents in infection control and are generated by very slow electrical anodic corrosion of a silver wire located closely adjacent the infection site. In particular, a silver anode and a cathode of non-corroding metal are located in an electrolytic nutrient medium with the silver anode being within five millimeters of the infection site, and a direct voltage is applied to the anode and cathode in a manner passing a positive current in the microampere range into the silver anode causing it to corrode slightly and give off silver ions which produce a germicidal environment about the infection site.

6 Claims, 1 Drawing Figure

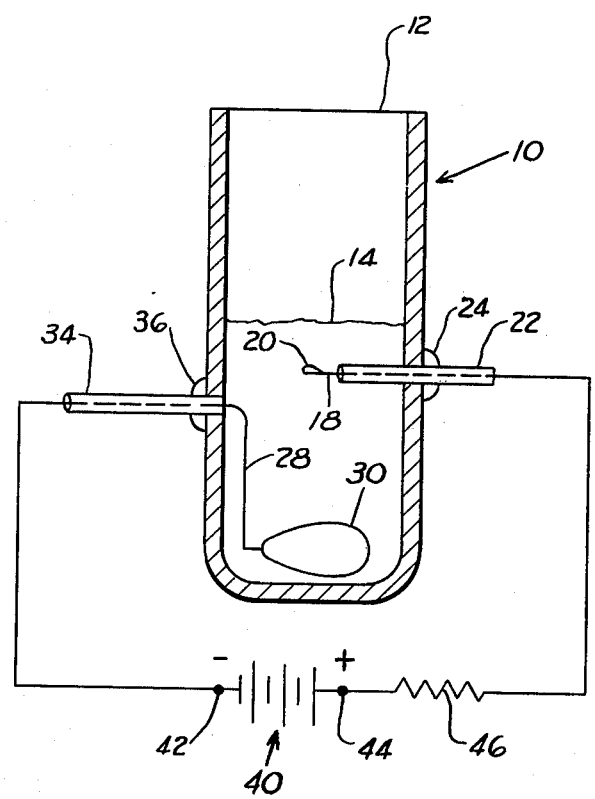

METHOD FOR ELECTRONIC CONTROL OF INFECTIONS USING SILVER IONS

BACKGROUND OF THE INVENTION

This invention relates to electronic control of infection, and more particularly to a new and improved electronic method and apparatus for killing plant and animal bacteria and plant viroids.

Nearly a century of experience has demonstrated the effectiveness of silver metal and silver salts against infection. Bolton in 1894 and Halstead in 1913 described the use of silver foil on fresh wounds to inhibit the growth of microorganisms, and argerol and silver nitrate were common bactericidal agents a decade or two ago.

The results have never been spectacular and silver therapy has drifted out of clinical use. The very low solubility of silver and of many silver salts in aqueous solution permits only a very low concentration of the Ag+ ion. Spadero in 1974 showed this highly oxidizing ion to be the effective germicidal agent, demonstrated a much higher concentration of the ion by anodically corroding metallic silver, and reported killing a broad spectrum of animal bacteria with as little as 400 nanoamperes of anodic DC current.

SUMMARY OF THE INVENTION

It is, therefore, a primary object of this invention to provide a new and improved method and apparatus for electronic control of infection.

It is a further object of this invention to provide an electronic method and apparatus for killing of plant and animal bacteria and plant viroids.

It is a more particular object of this invention to provide a method and apparatus for killing of plant and animal bacteria and plant viroids by electrically generated silver ions.

It is a further object of this invention to provide such a method and apparatus for killing plant bacteria and plant viroids without damage to the host plant.

It is a further object of this invention to provide such a method and apparatus for killing animal bacteria with a lower current than heretofore employed.

The present invention provides a method and apparatus for killing plant and animal bacteria and plant viroids by electrically generated silver ions. The silver ions serve as germicidal agents in infection control and are generated by very slow electrical anodic corrosion of a silver wire located closely adjacent the infection site. In particular, a silver anode and a cathode of non-corroding metal are located in an electrolytic nutrient medium with the silver anode being within about five millimeters of the infection site, and a direct voltage is applied to the anode and cathode in a manner passing a positive current in the microampere range into the silver anode causing it to corrode slightly and give off silver ions which produce a germicidal environment about the infection site.

The foregoing and additional advantages and characterizing features of the present invention will become clearly apparent upon a reading of the ensuing detailed description together with the included drawing wherein:

BRIEF DESCRIPTION OF THE DRAWING

The single FIGURE of the drawing is a diagrammatic view illustrating the method and apparatus of the present invention.

DETAILED DESCRIPTION OF THE ILLUSTRATED EMBODIMENTS

The method and apparatus of the present invention employs electrically generated silver ions for killing plant and animal bacteria and plant viroids. One area of use of the present invention is electronic control of plant infection in the production of disease-free plant clones.

Normal plant reproduction from seeds may or may not produce offspring identical to the parent. Also, infected parent stock may pass the infection to the offspring through the seed.

In recent years a new method of reproduction, called cloning, has alleviated some of these problems. A microscopic piece of leaf or root is sterilized in a weak bleach solution and then placed in a richly nutrient, warm medium. Under these conditions, the cell's normal growth pattern of root and leaf development is suppressed. Instead, the cells of the sample divide into a sheet of clusters, each with the genetic DNA code of its parent. At some point, a cluster can be excised out and allowed to grow normal roots and leaves. Each resulting plant will be identical to its original parent. Thus, cloning provides a new method of producing large numbers of identical, healthy plants from a single sample.

However, occasionally, bacterial infection may survive the bleach solution and be introduced into the culture medium. The offspring will then become infected. It therefore would be highly desirable to provide a method and apparatus to electronically control plant infections.

Referring now to the single FIGURE of the drawing the apparatus of the present invention includes a container, which in the illustrative apparatus is a Pyrex test tube 10 having an opening 12 at one end, for holding or containing a quantity of liquid 14 in the form of an electrolytic nutrient medium. The apparatus further comprises an anode 18 of pure silver, or of an alloy from which silver can be anodically liberated, located in the medium 14 and closely adjacent the infection site. Anode 18 preferably is in the form of a thin silver wire with a formation 20 such as a small loop at the end thereof for holding the plant clone in the medium 14 in a manner which will be described. In the apparatus shown, anode wire 18 is partially contained in or surrounded by a protective tubing or sleeve 22 which is fitted through an opening provided in the wall of container 10. The junction between tubing 22 and the container wall is provided with an appropriate seal 24. Tubing 22 extends along a major portion of the length of the wire 18 within container 10 and terminates a short distance from the loop formation 20. The tubing 22 also extends along a significant portion of wire 18 external to container 10.

The apparatus of the present invention further comprises a cathode 28 of non-corroding metal located in the medium 14 and spaced from the infection site. Cathode 28 may also be of silver. Silver is non-corroding when cathodically protected. Platinum also is a satisfactory cathode metal. Cathode 28 preferably is in the form of a thin wire which in the apparatus shown extends into the medium 14 for a considerable distance and terminates in a formation 30 such as a loop of significantly greater size than the anode loop formation. In the illustrative apparatus, a portion of the length of cathode wire 28 external to container 10 is surrounded by a protective tubing or sleeve 34. One end of sleeve 34 abuts the wall of the test tube 10 adjacent an opening in the wall through which cathode wire 28 extends. The junction between the end of tubing 34 and the container wall is provided with an appropriate seal 36.

The apparatus of the present invention further comprises means for applying to the anode 18 a positive electric current in the microampere range. There is provided a source of direct voltage in the form of battery 40 having negative and positive terminals 42 and 44, respectively. Negative terminal 42 is connected directly to cathode 28. Positive terminal 44 is connected through a current-limiting resistor 46 to the anode 18. By way of example, in an illustrative apparatus, source 40 is a six volt battery and resistor 46 has a magnitude of 2.7 megohms. A constant current electronic circuit comprising the combination of a field effect transistor and a fixed resistor can be substituted for resistor 46. The transistor source terminal would be connected to battery terminal 44, and anode 18 would be connected to the transistor gate terminal and through the fixed resistor to the transistor drain terminal.

In operation, the electrodes 18 and 28 are electrically driven in the plant culture medium 14. In particular, liquid 14 can comprise an agar medium, and the anode 18 is located within about 5.0 millimeters of the plant clone. As the positive current in the microampere range is passed through the silver anode 18, the current causes the anode to corrode slightly and give off silver ions. These silver ions produce a germicidal environment about the clone, killing any bacteria present and arresting the reproduction of new bacteria. After a number of hours or days of this treatment, the clone will become disease-free and develop into a normal disease-free offspring, even though its parent plant was infected.

The method and apparatus of the present invention is illustrated further by the following examples:

EXAMPLE I

Three identical arrangements of apparatus were set-up to the foregoing description and as shown in the drawing. The holes or apertures in the Pyrex test tubes were made by piercing the tubes with a butane touch. Silver wires were inserted through the holes in each of the tubes, and the protective tubes or sleeves were of silicone rubber. The protective tubes were sealed to the glass test tubes with Dow Corning type "A", medical adhesive. The silver wires defining the cathodes in each arrangement had a diameter of 0.020 inch an were formed into the bottom of each test tube in a single loop. The silver wires defining the anodes in each arrangement had a diameter of 0.010 inch and were brought to the center of each test tube and terminated in a small loop. The battery voltage was 6.0 volts and the resistor magnitude 2.7 megohms.

Each apparatus arrangement was sterilized in a steam autoclave, and then a nutrient medium was introduced into each test tube in an amount sufficient to cover the anode loop. The nutrient medium was Murashiga shoot multiplication medium A available from Grand Island Biological Co. under the number 500-119. A microscopic sample of *ficus elastica* (rubber plant) was infected with a gram negative bacteria and placed on the anode loop. The electrical current into the anode wire was approximately 2 microamperes d.c.

Previous preparations without the foregoing electronic excitation had shown overnight growth of bacterial colonies about the clone. The three examples with electronic excitation showed no bacterial clouds. Their growth continued on to produce disease free plants. The foregoing evidences laboratory production of disease free offspring from infected plant stock by the method and apparatus of the present invention.

EXAMPLE II

The procedure of Example I was repeated, using one millimeter of leaf tissue taken from a *ficus elastica* (rubber plant) known to be infected by an unknown bacteria. All previous attempts to get an uninfected clone from this parent had failed. The clone was placed in the nutrient solution resting on the anode loop of the pure silver wire. About one microampere of positive current was delivered to the anode for 24 hours. On repeated tests, currents ranging from 0.1 to 10 microamperes were used. In ten trials, the uninfected daughters were cloned from the infected parent. No appreciable difference was seen at the different current levels.

EXAMPLE III

Seven samples of *ficus elastica* (rubber plant) from a parent known to be infected were set up in nutrient agar solution at 37° C. In particular, group A consisted of three plant clones in test tubes with new silver wires, electrically stimulated as described in Example I. Group B consisted of two plant clones in test tubes set up as in Example I, but with old wires, i.e. not stimulated at this time but previously stimulated at some earlier time. Group C consisted of two plant clones in test tubes with no electrodes and therefore served as a control group. Electrical current was supplied to Group A according to the procedure of Example I for 92.5 hours. When the electrical current was turned off, the control group showed contamination and both groups A and B were clear. Seven days after the electrical current was turned off, all three groups showed contamination. Thus, the presence of stimulated or formerly stimulated electrodes delayed the appearance of bacteria well beyond its appearance in the control group.

EXAMPLE IV

Ficus elastica bacteria in the form of a gram negative rod of unknown type were cultered into agar onto a Petri dish provided with five silver wire anodes and a common silver wire cathode. The results are summarized in Table I as follows:

TABLE I

| Electrode Number | Measured Anode Current @ 25° C. | Results | Anode Color |
|---|---|---|---|
| 1 | 2.479 uA | cleared area 22mm × 10mm | black |
| 2 | 0.734 uA | cleared area 15mm × 10mm | black |
| 3 | 0.732 uA | cleared area 17mm × 10mm | black |
| 4 | 0 | no cleared area | bright |
| 5 | 0 | no cleared area | bright |

As indicated, the currents are in microamperes. Cleared area indicates killing of bacteria, and lack of clearing indicates no killing of bacteria. Thus the germicidal effect on these unknown plant bacteria is confirmed.

EXAMPLE V

The procedure of Experiment IV was repeated using bacteria from infected raspberry plants. This was a gram negative diplo-cocci of unknown type. The results were the same as for Experiment IV. All three stimulated electrodes killed the bacteria and the residual effect from unstimulated, used electrodes also killed the bacteria. The unstimulated, new electrodes, i.e. electrodes nos. 4 and 5, showed no cleared area indicating no killing.

The foregoing establishes that the method and apparatus of the present invention provides a germicidal effect on plant bacteria by means of electrically stimulated silver anodes, and the foregoing also indicates that residual effects from recently stimulated electrodes also are germicidal. In both approaches, there was no apparent damage to the host plant.

A related consideration is preventing or minimizing systemic infection of the parent plant. This may be achieved by the use of microscopic samples to attempt to get through silver ion infusion into the parent cells, by the use of longer term electrical stimulation to try to infuse the silver ions up into the plant capillaries, and by periodically pruning off all possible growth to excise infected material thereby leaving only sterile structure. Since small samples have much less probability of surviving, there may well be an optimum sample size with the best probability of survival balanced against the best probability of avoiding infection.

Another area of use of the method and apparatus of the present invention is control of non-bacterial pathogens such as tumor cells and virus infections which are not readily controlled by antibiotics or by conventional sterilizing techniques and in a manner which does not cause death to the host plant. In particular, there is a class of virus-like pathogens called viroids which are RNA structures having no protein encasement. The viroid is only 1/100th the size of a virus, and since it is a naked RNA structure without the protein sheath which characterizes a virus, the viroid is impervious to antibodies and can withstand boiling water for about twelve minutes without damage. It also seems to be able to withstand very low temperatures. The viroid has a very long incubation period of from about six months to several years. Six plant diseases have been traced to viroids which represent a real hazard to the California citrus industry and which also have been found in some New York State crops. One animal disease, i.e. scrapie in sheep, is now suspect.

The method and apparatus of the present invention as described herein and illustrated in the drawing was employed for the killing of a viroid pathogen as illustrated in the following example:

EXAMPLE VI

Using an apparatus arrangement similar to that illustrated in the drawing, a clone from a chrysanthemum known to be infected with a viroid (chrysanthemum stunt) was introduced into a modified Murashiga shoot media (GIBCO#500-1124) previously introduced to the container 10, with the clone resting on the pure silver anode wire loop 20. The cathode was a large-area pure silver helix rather than a single loop as shown in the drawing. About one microampere was passed through the silver anode all during the two-week growth period of the clone. The plant grew well and developed leaves and roots. At the conclusion of this time, the clone was pulverized, introduced into a gel and subjected to gel electrophoresis. No viroid band was seen, suggesting that the silver ion environment had killed the viroid pathogen. This is a preliminary result, subject to confirmation by repetition.

The foregoing accomplishment of the electrical killing of a viroid may assume considerable clinical importance should viroids be found associated with human disease. Even for use with plant reproduction techniques, the ability of the method and apparatus of the present invention to assure a non-infected clone from a viroid infected parent is of considerable economic importance.

Another area of use of the method and apparatus of the present invention is the electrical killing of animal bacteria by anodically generated silver ions using extremely low current levels, for example as low as 25 nanoamperes d.c. This is illustrated in the following example:

EXAMPLE VII

Glass petri dishes were prepared by drilling six to eight holes through the sides with $CO_2$ laser or with a butane micro-torch. A pure silver anode wire, insulated by a silicone sheath, was inserted through each hole and sealed in place with silicone cement such as Dow Corning medical adhesive "A". The wires were 0.010 inch in diameter. Two cm of the length of each wire extended beyond the silicone sheath. A large-area central helix of pure silver having a diameter of 0.020 inch and a length of about 10 cm served as a common cathode. Each anode wire was connected through a current-limiting resistor to the positive terminal of a six volt battery. This provided a different level of current to each anode. One or two anodes were always left unconnected, i.e. zero current, as controls.

The dishes were sterilized by autoclave and then filled about 5 mm deep with a sterile agar preparation. An animal bacteria culture was then introduced and allowed to grow for 24 hours at 37° C., producing a semi opaque cloud of bacterial colonies. With some trials new clean wires were used and the battery was connected after bacterial growth was complete. With others, the battery was connected immediately upon innoculation of the media. With still others, used dishes were cleared of media, washed, autoclaved and refilled with new media. The current was measured with a digital microammeter in some cases and calculated in others from voltage and resistor data, making suitable allowance for some voltage polarization loss at the metal/media interface.

The results were as follows: With new wires, cleared areas (killed bacteria) developed within 24 hours out to 5 mm from each stimulated anode. No clearing developed about the cathode, and no clearing developed about new unstimulated anodes. Residual clearing developed about previously stimulated anodes which were rerun a second time in new media. Some clearing was observed as low as 25 nanoamperes. More clearing was developed by higher currents. Above 100 nanoamperes only modestly larger areas were cleared. At 1000 nanoamperes only about 10% more area was cleared that at 100 nanoamperes. When stimulation was applied immediately upon innoculation, areas within 5 mm of stimulated anodes remained clear.

Based upon these results, it is concluded that bactericidal action seemed due to Ag+ ion, was confined to stimulated anodes, and thus would seem to be a chemical rather than an electrical field effect. Bactericidal action was more or less linear up to 100 nanoamperes (with the 0.01"D×2 cm long electrodes) but nearly independent of current above that. Some bactericidal action was seen at a current level as low as 25 nanoamperes. Thus, the method and apparatus of the present invention is useful in the electrical killing of animal bacteria by anodically generated silver ions using current levels as low as 25 nanoamperes.

The electrically generated silver ions, employed in the method and apparatus of the present invention, are far more effective as germicidal agents than simple addition of silver salts. Silver chloride, for example, is only sparingly soluble and a solution of silver chloride does not have very many Ag+ ions. However, electrolytic corrosion of silver produces copius amounts of Ag+ ion which is a powerful oxidizer. Although this high concentration will eventually equilibrate to normal solution values on a time constant, the bactericidal action will be complete by then.

It is therefore apparent that the present invention accomplishes its intended objects. Electrical killing of plant bacteria is accomplished by means of anodically generated silver ions without damage to the host plant. Electrical killing of a plant viroid is accomplished by means of anodically generated silver ions with no apparent damage to the host plant. Electrical killing of animal bacteria by anodically generated silver ions is accomplished with current levels as low as 25 nanoamperes. While the system of the present invention has been described in connection with killing plant and animal bacteria and plant viroids it is believed that the system also will work with plant and animal viruses, as well as with animal tumors and with floating malignancies such as ascites tumors or leukemia. While several embodiments of the present invention have been described in detail, this is for the purpose of illustration, not limitation.

I claim:

1. A method of killing plant bacteria and plant viroids to control plant infection while growing plant cells comprising the steps of:
   (a) placing a quantity of host plant tissue in an electrolyte nutrient medium; and
   (b) treating said host plant tissue with anodically generated silver ions in said medium in an amount sufficient to kill plant bacteria and plant viroids without causing damage to said host plant tissue.

2. A method according to claim 1, wherein said step of treating comprises placing a silver anode in said medium in close proximity to said plant tissue and passing a positive electrical current through said anode in a manner causing said anode to corrode slightly and release silver ions to produce a germicidal environment at the infection site in said plant tissue.

3. A method according to claim 2, wherein the magnitude of said electrical current is in the microampere or nanoampere range.

4. A method according to claim 1, wherein said step of treating comprises placing in said medium in close proximity to said plant tissue a silver member previously and recently subjected to electrical stimulation such that said member releases silver ions into said medium to produce a germicidal environment at the infection site in said plant tissue.

5. A method according to claim 1, wherein said plant tissue is a plant clone whereby a disease-free plant offspring is produced.

6. A method of killing animal bacteria to control infection while growing animal cells comprising the steps of:
   (a) placing a quantity of host animal tissue in an electrolytic nutrient medium; and
   (b) treating said host animal tissue with anodically generated silver ions in said medium in an amount sufficient to kill animal bacteria without causing damage to said host animal tissue, said silver ions being generated by passing a positive electrical current having a magnitude less than 400 nanoamperes through a silver anode.

* * * * *